(12) United States Patent
Schneider et al.

(10) Patent No.: US 9,625,400 B2
(45) Date of Patent: Apr. 18, 2017

(54) METHOD FOR SETTING A TEMPERATURE OF A SENSOR ELEMENT

(75) Inventors: Jens Schneider, Leonberg (DE);
Michael Fey, Wiernsheim (DE);
Ingmar Burak, Stuttgart (DE); Markus Riemann, Vaihingen/Enz (DE);
Reinhard Hamann, Bietigheim-Bissingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 544 days.

(21) Appl. No.: 13/877,448

(22) PCT Filed: Sep. 23, 2011

(86) PCT No.: PCT/EP2011/066595
§ 371 (c)(1),
(2), (4) Date: Aug. 23, 2013

(87) PCT Pub. No.: WO2012/045599
PCT Pub. Date: Apr. 12, 2012

(65) Prior Publication Data
US 2013/0327124 A1 Dec. 12, 2013

(30) Foreign Application Priority Data

Oct. 6, 2010 (DE) .......... 10 2010 042 013

(51) Int. Cl.
*G01N 25/18* (2006.01)
*G01N 27/406* (2006.01)
(Continued)

(52) U.S. Cl.
CPC ........... *G01N 25/18* (2013.01); *F01N 11/007* (2013.01); *G01N 27/4067* (2013.01);
(Continued)

(58) Field of Classification Search
CPC ... F01N 11/007; F01N 2560/20; G01N 25/18; G05D 23/24
(Continued)

(56) References Cited

U.S. PATENT DOCUMENTS 5,287,281 A * 2/1994 Meaney ................. B60K 28/16
123/1 A
5,916,130 A * 6/1999 Nakae ..................... B60K 6/365
123/568.16
(Continued)

FOREIGN PATENT DOCUMENTS

CN 101535799 9/2009
CN 102257383 11/2011
(Continued)

OTHER PUBLICATIONS

International Search Report for PCT/EP2011/065595, dated Nov. 28, 2011.
(Continued)

*Primary Examiner* — Hezron E Williams
*Assistant Examiner* — Gedeon M Kidanu
(74) *Attorney, Agent, or Firm* — Gerard Messina (57) ABSTRACT

A method for setting a temperature of a sensor element, which is heatable with the aid of a heating device, for detecting at least one property of a gas in a measuring gas chamber includes at least one regulation of the heating device, the regulation including: (a) detecting at least one actual value of at least one controlled variable of the sensor element, (b) ascertaining a setpoint value of the at least one controlled variable, (c) generating at least one manipulated variable of the heating device with the aid of a comparison of the setpoint value and the actual value, and (d) in a monitoring step, checking at least one parameter used to set
(Continued)

the temperature, and the at least one manipulated variable being influenced as a function of the check.

14 Claims, 4 Drawing Sheets

(51) Int. Cl.
    *F01N 11/00*     (2006.01)
    *G05D 23/24*     (2006.01)

(52) U.S. Cl.
    CPC .......... *G05D 23/24* (2013.01); *F01N 2560/20* (2013.01); *Y02T 10/47* (2013.01)

(58) Field of Classification Search
    USPC ............................................................. 73/25
    See application file for complete search history.

(56) References Cited

U.S. PATENT DOCUMENTS

| | | | | |
|---|---|---|---|---|
| 5,974,857 | A * | 11/1999 | Yamashita | G01N 27/4067 73/23.32 |
| 8,140,246 | B1 * | 3/2012 | Manchanda | F01P 11/16 123/41.15 |
| 8,721,854 | B2 * | 5/2014 | Aoki | G01N 27/4065 204/410 |
| 8,873,545 | B2 | 10/2014 | Ozawa | |
| 2007/0119435 | A1 * | 5/2007 | Carter | F02D 19/12 123/585 |
| 2007/0149349 | A1 * | 6/2007 | Utsumi | B60K 6/445 477/3 |
| 2007/0214774 | A1 * | 9/2007 | Higuchi | F02D 41/025 60/285 |
| 2007/0215470 | A1 * | 9/2007 | Kawase | G01N 27/4065 204/424 |
| 2007/0282558 | A1 * | 12/2007 | Sagisaka | B62D 5/049 702/116 |
| 2007/0284248 | A1 * | 12/2007 | Kawase | F02D 41/1454 204/424 |
| 2010/0031731 | A1 * | 2/2010 | Kawase | G01N 27/4065 73/23.32 |
| 2013/0199283 | A1 * | 8/2013 | Chen | F02D 41/008 73/114.73 |
| 2013/0327124 | A1 * | 12/2013 | Schneider | F01N 11/007 73/25.01 |
| 2014/0346041 | A1 * | 11/2014 | Nishijima | G01N 27/4067 204/408 |

FOREIGN PATENT DOCUMENTS

| | | | |
|---|---|---|---|
| CN | 102362175 | | 2/2012 |
| DE | 10 2006 053808 | | 5/2008 |
| DE | 10 2007 001 562 | | 7/2008 |
| DE | 10 2009 001 242 | | 9/2010 |
| JP | 2-285245 | | 11/1990 |
| JP | 3-19957 | | 2/1991 |
| JP | H 1026599 | | 1/1998 |
| JP | 1088227 | A | 4/1998 |
| JP | 11107830 | A | 4/1999 |
| JP | 2001330580 | A | 11/2001 |
| JP | 2005-2974 | | 1/2005 |
| JP | 2005-195368 | | 7/2005 |
| JP | 2006153601 | A | 6/2006 |
| JP | 2009-0074884 | | 3/2009 |
| JP | 55-45224 | | 7/2014 |
| JP | EP 2816350 A1 * | 12/2014 | ......... G01N 27/4067 |
| WO | WO 2010/072490 | | 7/2010 |
| WO | WO 2010/108732 | | 9/2010 |

OTHER PUBLICATIONS

"Sensors in Motor Vehicles", Robert Bosch GmbH, 2007 ed., pp. 154-159.

* cited by examiner

METHOD FOR SETTING A TEMPERATURE OF A SENSOR ELEMENT

BACKGROUND OF THE INVENTION

1. Field of the Invention

The present invention relates to a method for setting a temperature of a sensor element.

2. Description of the Related Art

A multitude of sensor elements for detecting at least one characteristic of a gas in a measuring gas chamber are known from the related art. In principle, this may be any arbitrary characteristic of the gas, for example, a physical and/or chemical characteristic of the gas. In particular, the present invention is described hereafter with reference to sensor elements for detecting a fraction, i.e., for example, a partial pressure and/or a percentage, of at least one gas component in the gas. The gas component may be oxygen in particular. Other gas components may also alternatively or additionally be detected, however, for example, nitrogen oxides, hydrocarbons, or other gas components. However, the present invention is not restricted to the detection of gas components, but rather in principle, alternatively or additionally, other characteristics of the gas may also be detected.

In particular, sensor elements which are based on the use of at least one solid electrolyte, i.e., an ion-conducting solid, for example, an oxygen ion-conducting solid, are used to detect gas components. Such solid electrolytes may be prepared, for example, based on zirconium dioxide, for example, yttrium-stabilized zirconium dioxide and/or scandium-doped zirconium dioxide. Such sensor elements are used, for example, in the automotive field to detect gas components in the exhaust gas of an internal combustion machine having at least one engine. Examples of such sensor elements are described in Robert Bosch GmbH: Sensoren im Kraftfahrzeug [Sensors in Motor Vehicles], 2007 edition, pages 154-159. The sensor elements described therein may also in principle be operated as per a method according to the present invention and/or used within the scope of a sensor device according to the present invention.

A lambda sensor is generally based on the use of at least one galvanic oxygen concentration cell having at least one solid electrolyte. Alternatively or additionally, so-called pump cells may also be used. Lambda sensors may have a single cell or also a multi-cell construction, reference also being able to be made to the cited related art as an example. Such sensor elements generally have at least one heating device. The solid electrolyte thus generally becomes conductive to oxygen ions at an activation temperature of approximately 350° C. The nominal temperature of normal lambda sensors is generally significantly higher, for example, at 650° C.-850° C. In order to achieve the nominal temperature independently of the ambient conditions, for example, the temperature of the exhaust gas, the sensor element is generally actively electrically heated. For this reason, most sensor elements of the mentioned type have at least one electrical heating element, which is also referred to hereafter in general as a heating device and which is generally activated by at least one control unit. For example, known lambda sensors based on zirconium dioxide have an integrated platinum heater, which is generally designed in such a way that it has a greater heating power reserve under normal operating conditions. This means that the heater voltage or heating power required for the operation of the sensor element is generally significantly lower than the available supply voltage or supply power. For example, in typical sensor elements of the above-mentioned type, operating temperatures of 780° C. are already reached at heater voltages of less than 8 V. In many cases, the sensor element is not operated using a DC voltage, but rather using a clocked effective voltage, which is generated by pulse width modulation of a higher DC voltage (battery voltage). Accordingly, the concept of a heater voltage may be understood hereafter as both the actual voltage, which is applied to the heating device, and also alternatively an effective voltage.

The output signal of a sensor element of the above-mentioned type is generally functionally heavily dependent on the temperature of the sensor element. To improve the signal accuracy, decoupling the temperature of the sensor element from changes in the exhaust gas temperature and keeping it as constant as possible are therefore to be sought. For example, a temperature control of the heater voltage of a discrete-level sensor via a characteristics map as a function of an operating point using the input variables of an exhaust gas temperature and an exhaust gas mass flow rate is routine. Increased temperature accuracy results through a temperature regulation of the sensor element. For example, an internal resistance $R_i$ of the sensor element may be used as the controlled variable, for example, of at least one cell of the sensor element, since there is generally an unambiguous relationship between the internal resistance and the temperature of the sensor element. For example, in commercially available discrete-level sensors, an internal resistance of 220Ω corresponds to a sensor element temperature of 780° C. A corresponding temperature regulation is also used in broadband sensors.

In spite of the improvement of the signal accuracies through existing regulations, demand and improvement potential still exist for more exact temperature settings, to further improve the signal accuracy of the sensor element. In particular, the operating temperature of the sensor element is to be settable independently of the exhaust gas temperature, to further increase the signal accuracy and therefore in turn allow lower emissions and more robust diagnoses. At the same time, an activation having a high heating power reserve is to be made possible, without the risk existing of destroying the sensor element by overheating upon heating in the fundamental additional vehicle electrical system voltage range. Furthermore, the sensor element of an exhaust gas sensor is to be operable at the most constant possible temperature and is to be protected from overheating at the same time.

BRIEF SUMMARY OF THE INVENTION

To improve known sensor elements and methods for operating these sensor elements and to at least partially implement the above-mentioned goals, a method for setting a temperature of a sensor element, which is heatable with the aid of a heating device, for detecting at least one characteristic of a gas in a measuring gas chamber and a sensor device for detecting at least one characteristic of a gas in a measuring gas chamber are accordingly proposed. As described above, the detection of the at least one characteristic may in particular be a determination of a fraction of a gas component in the gas. The gas component may in particular be one or more of the gas components oxygen, nitrogen, nitrogen oxides, hydrocarbons, or other components. The gas may in particular be an exhaust gas, in particular an exhaust gas of an internal combustion engine, and the measuring gas chamber may in particular be an exhaust system, for example, an exhaust system in a motor vehicle. However, other fields of application are also possible in principle.

The method is used to set a temperature of the sensor element, which is heatable with the aid of a heating device. A setting of a temperature may be understood as a setting to a fixedly predefined temperature or also to a variably predefined temperature, temperature curves also being predefinable. A control and/or a regulation of the temperature may also be subsumed under a setting, as explained in greater detail hereafter. The heating device may in particular include a resistive heating device, i.e., for example, at least one heating resistor, which may be resistively heatable by application of a heater voltage and/or a heater current, for example. The proposed method includes the method steps described hereafter, which may preferably, but not necessarily, be carried out in the described sequence. Individual or multiple method steps may also be carried out in parallel in time, overlapping in time, or repeated individually or in multiples, or carried out over longer periods of time. The method may additionally include further method steps which are not listed.

In a first method step, at least one actual value of at least one controlled variable of the sensor element is detected. A controlled variable may be understood in principle as any arbitrary measured variable of the sensor element, which is relevant for the temperature setting, in particular an electrical and/or thermal measured variable which correlates directly or indirectly with the temperature, i.e., a measured variable which allows an inference to an instantaneous temperature of the sensor element or a range of the sensor element. Examples of controlled variables will be explained in greater detail hereafter. Instead of the actual measured variable, variables derived from this measured variable may also be used, for example, interpolated, extrapolated, filtered, amplified, digitized, or other values. An actual value of the at least one controlled variable is understood as an instantaneous value, i.e., a measured value or a value of the controlled variable derived from the measured value, which has been detected at the present point in time or at a point in time which dates back preferably not more than a few seconds, for example, not more than 10 seconds, in particular not more than 5 seconds, preferably not more than 1 second, or even not more than 100 ms.

In another method step, at least one setpoint value of the at least one controlled variable is ascertained. A setpoint value is understood as a value of the controlled variable to which the controlled variable is to be set exactly or with specification of one or more tolerance thresholds. The ascertainment of the setpoint value may take place in particular in that this setpoint value is provided by a device separate from the sensor element, for example, in which this setpoint value is fixedly predefined or, as explained in greater detail hereafter, is determined in consideration of at least one control variable, which characterizes the influence of surroundings of the sensor element on the temperature of the sensor element. To ascertain the setpoint value, accordingly, for example, at least one data processing device and/or at least one electronic table and/or another type of device may be provided, which ascertains the at least one setpoint value and provides it for the method.

In another method step, at least one manipulated variable of the heating device is generated with the aid of at least one comparison of the setpoint value and the actual value. A manipulated variable is to be understood as a variable, preferably an electrical signal and/or digital information, with the aid of which the heating device may be directly or indirectly activated. This manipulated variable may thus include, for example, as explained in greater detail hereafter, for example, a heating power, a heater voltage (instantaneous or also effective heater voltages being able to be used), a heating current, or similar variables, which may be directly applied to the heating device. Alternatively or additionally, the at least one manipulated variable may optionally also be designed in such a way, however, that it must initially be further processed, before it is applied to the heating device, for example, at least one final control element (for example, at least one heating voltage generator and/or at least one amplifier) being able to be used.

In another method step, at least one monitoring step is carried out. In this monitoring step, at least one parameter, which is used to set the temperature with the aid of the proposed method, is checked and the at least one manipulated variable is influenced as a function of the check. In principle, one or more of the above-mentioned and/or further variables used in the method according to the present invention may be used as a parameter used to set the temperature. In particular, the at least one parameter may be a parameter used during the regulation and/or an optionally superimposed control, which is explained in greater detail hereafter, optionally also the manipulated variable itself. Examples of parameters used for the setting of the temperature are explained in greater detail hereafter. Checking may be understood in particular, as explained in greater detail hereafter, as a query of whether or not the at least one parameter fulfills at least one predefined condition. For example, as explained in greater detail hereafter, one or more threshold value conditions may be predefined. Influencing the at least one manipulated variable as a function of the check may be understood as direct or indirect influence of the manipulated variable, for example, in that the manipulated variable or an added variable acting on the manipulated variable is changed in a targeted way. The influence may include a change, for example, a change with the aid of one or more correction functions, correction characteristic curves, correction factors, with the aid of a subtraction and/or an addition of a predefined absolute value, with the aid of a replacement by a default value, in particular 0 or a maximum value or minimum value, or also—depending on the result of the check of the at least one parameter—leaving the at least one manipulated variable unchanged. Instead of a single condition, multiple conditions may also be predefined, which may also be coupled to different types of influences, for example. Thus, for example, multiple checks may be carried out, each check or each group of checks resulting in a different influence of the at least one manipulated variable.

After carrying out the mentioned method steps, in particular the at least one manipulated variable and/or at least one further manipulated variable derived from the manipulated variable, for example, with one or more final control elements interposed, may be applied to the heating device. The correction of the manipulated variable preferably occurs before the application to the heating device.

It is particularly preferable if the method is carried out in such a way that furthermore at least one control variable is detected. A control variable is to be understood as an arbitrary variable which characterizes an influence of surroundings of the sensor element on the temperature of the sensor element. In particular, the control variable may include at least one of the following parameters: an ambient temperature of the sensor element, in particular a gas temperature, for example, an exhaust gas temperature in the measuring gas chamber; an operating parameter of a device which contains, generates, or uses the gas, in particular an operating range of an internal combustion engine, preferably an engine operating point; a parameter which characterizes, in particular quantifies, a gas flow occurring in the surroundings of the sensor element, for example a volume flow rate and/or a mass flow rate of the gas, for example the exhaust gas; a parameter which characterizes, in particular quantifies, a temperature occurring in the surroundings of the sensor element, in particular an exhaust gas temperature, a catalytic converter temperature, and/or a pipe wall temperature, an engine speed, or an engine load state. This at least one control variable is generally already detected in present exhaust systems in motor vehicles, since, for example, exhaust gas temperatures are significant for the operation of catalytic converters, since engine operating points are detected by an engine controller in any case, and since exhaust gas flow rates (mass flow rates and/or volume flow rates) are also significant in exhaust gas recirculation, for example. In this regard, for example, parameters or combinations of such parameters which are detected in any case may be used as the control variables for the proposed method. However, other parameters are also alternatively or additionally usable.

As described above, the proposed method includes a regulation of the heating device. This regulation may optionally be superimposed on at least one control of the heating device. While at least one manipulated variable is generated in the case of a regulation based on a comparison of the setpoint value and the actual value, preferably automatically, a feedback being able to result with a closed sphere, in the case of a control, only a control reference variable is predefined, which is converted in the control into a corresponding control manipulated variable, without a closed sphere being used. The at least one control manipulated variable generated during the control may be superimposed on the manipulated variable generated during the regulation, for example, by addition, multiplication, subtraction, or in another way. Such superpositions are known in principle from the related art. For example, a different amplification of the manipulated variables generated during the regulation and during the control may take place before the superposition. Other types of superposition are also possible, however. The superposition may take place upstream or downstream from an optional final control element, for example, upstream or downstream from a heating voltage generator. Alternatively or additionally, different final control elements may also be used for the control and for the regulation, for example, in each case independent heating voltage generators, which each generate heating voltage independently of one another, which may subsequently be superimposed before they are applied to the at least one heating device.

The heating device may be controlled in particular in consideration of the at least one control variable, for example, one or more of the above-mentioned control variables, which characterize an influence of the surroundings of the sensor element on the temperature of the sensor element. In each case the same control variables or also different control variables may be used for the regulation and for the control.

The above-described setpoint value may be ascertained in particular in consideration of the at least one control variable. This means that the regulation may be adapted to the at least one control variable, which characterizes an influence of surroundings of the sensor element on the temperature of the sensor element. Alternatively or additionally, the control may also take place in consideration of the at least one control variable, for example, in that a control reference variable is selected in accordance with the at least one control variable. Thus, for example, the temperature of the gas in the measuring gas chamber and/or a flow of the gas in the measuring gas chamber may be taken into consideration. For example, if the exhaust gas temperature is high, a lower heating power is generally sufficient to set the temperature of the sensor element to the corresponding setpoint value, for example.

The at least one controlled variable may include in particular one or more of the following controlled variables: at least one internal resistance of the sensor element, in particular an internal resistance of at least one electrochemical cell of the sensor element, i.e., a combination of at least two electrodes and at least one solid electrolyte which connects the at least two electrodes; a temperature of the sensor element, which may be detectable with the aid of a separate temperature sensor, for example; a voltage between at least two electrodes of the sensor element, in particular between at least two electrodes of a Nernst cell of the sensor element; a current between at least two electrodes of the sensor element, in particular between at least two electrodes of a pump cell of the sensor element; for example, a current at a fixedly predefined pump voltage; an electrical resistance of a conductive structure, in particular a conductive structure of the sensor element, for example, an electrical resistance of a metal structure, for example, an electrical resistance of a feed line and/or a metallic meander. Other controlled variables or combinations of the mentioned and/or other controlled variables are conceivable. The use of at least one internal resistance or at least one variable which characterizes the internal resistance of the sensor element as the controlled variable is particularly preferred. For example, this internal resistance may also be measured in that a voltage and/or current pulse is briefly applied to at least one electrochemical cell of the sensor element and the particular other variable, for example, current or voltage, respectively, is measured. This internal resistance measurement may be carried out superimposed in time with other measurements of the sensor element for detecting the at least one characteristic of the gas or also intermittently, for example, in that the actual detection of the characteristic is briefly interrupted. Thus, for example, a cell which is actually used as a Nernst cell of the sensor element may briefly be used for a temperature measurement.

As described above, the manipulated variable may in particular be a manipulated variable which influences a heating power of the heating device and therefore an introduction of thermal energy into the sensor element. In particular, the manipulated variable may include one or more of the following manipulated variables: a heater voltage applied to the heating device; a heating power applied to the heating device; a heating current applied to the heating device; a parameter of a pulse width modulation of a heating power applied to the heating device. Combinations of the mentioned and/or other manipulated variables are also conceivable. The mentioned manipulated variables may be used directly or, as mentioned above, variables which may be derived from these manipulated variables or which generate these manipulated variables may be used.

As described above, in the monitoring step, at least one parameter used to set the temperature is checked. This at least one parameter may in particular include one or more of the following parameters: the actual value of the controlled variable, the setpoint value of the controlled variable, the manipulated variable; the control variable, which characterizes an influence of the surroundings of the sensor element on the temperature of the sensor element. Reference may be made to the above description in regard to the possible embodiments of the control variable. Alternatively or additionally, further parameters and/or combinations of the mentioned and/or other parameters may be used. In the monitoring step, the mentioned and/or other parameters may be checked as individual values, for example, in that an individual value comparison to at least one threshold value takes place. Alternatively or additionally, however, time curves of the parameters may also be checked for individual, multiple, or all of the mentioned parameters, for example, in that time variations, the history of the curve of the mentioned parameters, mean values of the mentioned parameters over a predefined period of time, filtered curves of the mentioned parameters, or other secondary parameters or functions, which are derived from the time curves of the mentioned parameters and/or other parameters, are analyzed. Examples will be explained in greater detail hereafter.

The checking of the parameter in the monitoring step may, as described above, be implemented in various ways, which may also be combined arbitrarily with one another. In particular, the checking of the parameter may include a query of whether the parameter (which is to be understood, as explained above, as an individual value, multiple values, derived values, time curves, or similar values) reaches, falls below, or exceeds at least one fixedly or dynamically predefined threshold value, and optionally if necessary how long this is the case. For example, at least one condition may read that the parameter is to fall below or is not to exceed a predefined threshold value. A condition that the parameter is to exceed or is not to fall below a predefined threshold value may also be predefined. The threshold value may be fixedly predefined or also variably, i.e., dynamically, for example, adapted to one or more external control variables and/or other external parameters. Alternatively or additionally, the checking may also include a query as to whether a time variation of the parameter over a measuring period of time falls below, reaches, or exceeds a predefined maximum variation and optionally if necessary how long this is the case. Certain conditions may accordingly also be set here with respect to the variations, again alternatively or additionally, the monitoring step may also include a check in the form of a comparison of a time curve of the parameter to at least one setpoint curve. Such a comparison may take place, for example, by a comparison of curves, functions, individual values, multiple values, or in a similar way. For example, deviations, error squares, correlation functions, or similar comparisons may be used to quantify a correspondence and/or a deviation of the curve from the setpoint curve. Combinations of the mentioned checks with one another and/or with other checks are also possible. Examples will be explained in greater detail hereafter.

Other preferred embodiments of the method relate to the type of the influence of the manipulated variable in the monitoring step. This influence may thus include in particular one or more of the influences described hereafter. For example, the influence may include a rejection of an individual value or multiple values of the parameter and/or an influence of the manipulated variable resulting therefrom. In particular, heavily varying time measured values of the parameter may be rejected, for example, measured values of the parameter which lie outside a predefined tolerance range, for example, a predefined tolerance range around a time mean value, may be rejected. Alternatively or additionally, filtering of the actual value and an influence of the manipulated variable resulting therefrom may take place. Filtering may take place, for example, with the aid of a low-pass filter and/or with the aid of a bandpass filter. Alternatively or additionally, the influence may in turn also include at least one averaging of the actual value and an influence of the manipulated variable resulting therefrom. Thus, for example, an actual value may be averaged over a certain period of time, for example, a geometric mean and/or an arithmetic mean being able to be formed. Alternatively or additionally, the manipulated variable may also in turn be replaced by a fixedly or dynamically predefined minimum value or maximum value. For example, a fixed lower limit and/or a fixed upper limit for the at least one manipulated variable may be predefined. A dynamic specification may occur as a deviation around a control manipulated variable, for example, if a control is superimposed on the regulation. Thus, for example, a tolerance range, within which the manipulated variable is to lie, may be predefined around a control manipulated value. Examples will be explained in greater detail hereafter. Alternatively or additionally, the manipulated variable may also in turn be set to a default value, for example, 0 or a value reduced in comparison to a maximum possible value. This may also take place by shutting down the application of heating energy to the heating device. Alternatively or additionally, the manipulated variable may in turn also be decreased by a predefined absolute value or a predefined correction factor. Alternatively or additionally, the manipulated variable may also be converted with the aid of at least one correction function into a changed manipulated variable. This at least one correction function may in principle include arbitrary corrections, for example, corrections with the aid of one or more correction values, correction functions, correction maps, or similar corrections known in principle to those skilled in the art. Alternatively or additionally, the influence may also include a change of at least one control loop of the setting of the temperature, in particular a shutdown of an integral component of the control loop. Alternatively or additionally, the influence may also in turn include a complete and/or partial shutdown of the regulation, for example, in that a complete switch-over is made to a control of the heating device, for example, a control of the above-described type.

In another aspect of the present invention, a sensor device for detecting at least one characteristic of a gas in a measuring gas chamber is proposed, in particular for determining a fraction of a gas component. The sensor device includes at least one sensor element for detecting the characteristic.

The sensor device also includes at least one heating device for heating at least a part of the sensor element. For example, the at least one heating device may be entirely or partially a component of the sensor element. Alternatively or additionally, however, the at least one heating device may also be entirely or partially accommodated in another way in the sensor device, for example, as an external component. In the first case, for example, the heating device may be integrated into a ceramic sensor element, for example, a layered structure of the ceramic sensor element, as is generally the case in planar sensors, for example. In the second case, the heating device may be designed as a rod heater, for example, as is generally the case in finger-type sensors, for example.

For example, the sensor element may be a sensor element having at least one solid electrolyte of the above-described type, in particular a ceramic solid electrolyte. The sensor element may in particular include one or more cells, i.e., two electrodes, which are connected to one another via the solid electrolyte. The sensor element may be designed as single-cell or also as multicelled. For example, reference may be made to the above-described related art in regard to possible embodiments of the sensor element. In principle, all types of sensor elements are usable according to the present invention, in particular ceramic sensor elements. Furthermore, the sensor device includes at least one activation device. The activation device is configured to carry out a method according to one or more of the preceding claims. The activation device may be designed centrally or also decentrally and may be implemented completely or partially in software and/or hardware. The activation device may also be entirely or partially implemented in a central engine controller, for example. The activation device may include a sensor activation device for activating and/or analyzing the sensor element or signals of the sensor element, for example. To implement the mentioned method, the activation device may also include, for example, at least one regulating device, which may contain at least one regulator, for example. To superimpose an optional control, the activation device may also include at least one control device. The regulating device and the control device may together form a heating element activation device.

The proposed method and the proposed sensor device have numerous advantages in relation to known methods and sensor devices. Thus, in particular, a sensor element having the characteristic of a high heating power reserve may be implemented, which could result in destruction of the sensor element by overheating upon heating in the onboard electrical system voltage range which is permissible in principle. This sensor element and the sensor device may be operated at constant temperature independently of the engine operating point, however, and may be configured at the same time in such a way that the sensor element may be protected from overheating. The method may be applied in principle to all actively heated and temperature-regulated or temperature-controlled exhaust gas sensors.

In order to keep the sensor element temperature as constant as possible, in particular a temperature control and a temperature regulation may be combined, as described above. For example, the control may be operated using a characteristics map, for example, in that one or more control variables are detected, as described above, which characterize the influence of the surroundings of the sensor element on the temperature of the sensor element. Such a control may be designed in particular as a characteristics map pilot control, which may be superimposed on the mentioned regulation. Such a superposition of a control with a regulation offers the advantage of high accuracy of a regulation, combined with a rapid reaction to changes in the engine operating point, for example, in the event of abrupt load changes, by the controls, which are preferably dependent on the operating point. High regulator travels are thus avoided, and the regulation may be used, for example, only to correct a control manipulated variable, which is generated by the control. The control manipulated variable is also referred to hereafter as a pilot control value. This method may be used in general for improved temperature stabilization. For the temperature regulation, in particular of a discrete-level sensor, in particular an internal resistance of a Nernst cell may be measured by a short-term current pulse between a measuring electrode and a reference electrode of the sensor element. This method is known in principle from the related art and is generally used therein, however, for diagnostic purposes. Within the scope of the above-proposed method, however, the internal resistance detected in this way may be used as the actual value of the at least one controlled variable of the sensor element or as a part of an actual value of the value. The ascertained internal resistance may be used for the regulation of the temperature. The disadvantage arising in conventional regulating methods in the event of inaccurate or erroneous detection of the controlled variable, that the operating temperature may exceed or fall below the optimum operating temperature, or that if the operating temperature is heavily exceeded, damage may even result on the sensor element, may be avoided by the proposed monitoring step, however. For example, if an increased contact resistance occurs permanently or temporarily in the signal circuit of the sensor element, for example, in the form of contacting problems, conventional temperature regulations have the tendency to regulate the high measured resistance to the lower target resistance and thus increase the heater voltage. The sensor element is thus operated excessively hot, and the heating device integrated into a sensor element may burn out. Thus, for example, conventional sensor elements are heated to a temperature of >1150° C., if they are operated for a long time at a heater voltage of 11 V, which results in burnout of the heater. The greater the heating power reserve of the heating device, in particular a heating device integrated into the sensor element, the greater the risk of damaging overheating of the sensor element. To avoid this overheating, in the method according to the present invention, the regulation of the temperature is provided, which may optionally be modified or assisted by one or more control variables, which may be provided by an engine control system, for example.

In the proposed method, in particular, as described above, a characteristics-map-based pilot control may be used in the superposition of the control, with which the proposed regulation may be superimposed or with which the proposed regulation may be combined in another way. This pilot control may be based in particular on measured or modeled control variables, which are also referred to as characteristic variables, for example, on measured or modeled characteristic variables of an exhaust system which well reflect the heating and cooling behavior of the sensor element which is dependent on the engine operating point. Since a fixed sensor element temperature generally corresponds to a fixed internal resistance of the sensor element, the superimposed regulation may be implemented, for example, as a PID regulator, which may compare measured internal resistance $R_i$ to a setpoint value, for example. In this way, a manipulated variable may be ascertained, which may output a heater voltage correction or a correction designed in another way of the heating power relative to the setpoint voltage of the pilot control, for example. Overheating of the sensor element due to erroneous internal resistance regulation is at least largely avoided by the countermeasures according to the present invention.

Examples of possible errors of an internal resistance regulation, which, without countermeasures, may result in overheating of the sensor element or burnout of the heating device, are:

(1) Erroneous internal resistance regulation due to the detection of inaccurate resistance measured values. Inaccurate resistance measured values may occur, for example, due to tolerance in an electrical circuit in a control unit, due to time-discrete and/or noncontinuous internal resistance measurement and/or due to measurement of the internal resistance during strong dynamic changes in the sensor element signal.

(2) Erroneous internal resistance regulation due to erroneous interpretation of the internal resistance measured values. A misinterpretation of the internal resistance measured values may occur, for example, if as a result of corrosion and/or aging, excessively large permanent or temporary contact resistances occur, for example, in a plug and/or wiring harness of the sensor element signal circuit.

(3) Erroneous internal resistance regulation due to temporarily elevated contact resistances in the heater circuit, for example, in the heating element activation device, for example, due to a loose contact.

A remedy against possible error (1) may be offered in particular by recognition and rejection of heavily varying time-adjacent measured values of the actual values. The recognition and/or the rejection of such outliers may in particular permit the sensor element internal resistance to only be measured in the event of a stable measuring situation, for example, only in the event of stable lambda, but not in the event of an unstable measuring situation, for example, in the event of lambda jumps, which may result in measuring errors. A further remedy against possible error (1) may be filtering of the measured values, for example, by a low-pass filter, time averaging, or a sliding mean value.

A remedy against possible errors (2) and/or (3) may be offered in particular by limiting the heater power, for example, the heater voltage and/or the heater current, and/or a corresponding influence of the pulse width modulation. This remedy may in turn be based in particular on measured and/or modeled characteristic variables of the exhaust system as the control variable. Through these one or more additional control variables, it may be possible in particular to predefine, as a function of the operating point, an upper limit and/or a corridor (i.e., defined upper and lower limits) for the manipulated variable, for example, the heater application, in particular the heater voltage, and therefore to reliably prevent overheating of the sensor.

Possible embodiments of the above-described monitoring step and the above-described influence may be in particular:

(a) Shutting down a sensor element heater (heater voltage 0 V) if one or more of the described parameters exceeds or falls below one or more limiting values. For example, the shutdown of a sensor element heater may be provided if a sensor element internal resistance reaches or falls below a critical threshold and/or the exhaust gas temperature and/or another control variable, which characterizes an influence of the surroundings of the sensor element on the temperature of the sensor element, reaches or exceeds a critical threshold.

(b) Reducing the at least one manipulated variable to a safe value, for example, a default value, if the at least one parameter reaches or exceeds or falls below a limiting value, for example, if the manipulated variable and/or the control variable exceeds or falls below or reaches a limiting value. For example, limiting of at least one application of heating energy to the heating device, for example, limiting of the heater voltage may be provided, so that a critical value may not be exceeded. It may also alternatively or additionally be provided that the application of heating energy to the heating device, for example, the heater voltage, is reduced if the exhaust gas temperature reaches and/or exceeds a critical threshold.

(c) Absolute limiting of the manipulated variable, for example, the variable controlling the heating power of the heating device, to a safe value if the at least one parameter, for example, the at least one control variable and/or the at least one manipulated variable, exceeds or falls below a limiting value for a certain time.

Therefore, it may be taken into consideration in particular that generally a certain value of the control variable and/or the manipulated variable may be noncritical in the short term, but may become critical if it is present for a longer time. This has been described above, since time curves may also be analyzed. In particular, a time after which a limitation is activated may advantageously be selected as a function of an instantaneous value of the at least one parameter, for example, the at least one control variable and/or the at least one manipulated variable. It may thus be taken into consideration that a higher value of the at least one parameter may result in overheating of the sensor even after a shorter time than a lower value, or vice versa. A further advantageous embodiment provides that the limitation may still be maintained for a certain time, even if the at least one parameter, for example, the at least one control variable and/or the at least one manipulated variable, briefly falls back into the noncritical range. A delayed reaction of the sensor element temperature to changes in the at least one parameter may thus be taken into consideration by suitably carrying out the monitoring step or the check. For example, it may be provided that the heater voltage or another type of application of heating energy to the heating device may be limited if it exceeds a critical value for a certain time. The time after which this limitation is activated may be a function of the instantaneous value of the heating power or the heating voltage or the parameter. The limitation may still be maintained for a certain time, also if the heater voltage or the heating power briefly falls back below the critical value, to take into consideration the delayed cooling of the sensor element after a reduction of the heater voltage.

(d) Relative limitation of the manipulated variable generated during the regulation to a control manipulated variable of the optionally superimposed control, for example, by a relative limitation of a heater voltage in relation to a pilot control heater voltage. This may be carried out in such a way that the at least one manipulated variable resulting from the combination of the superimposed control and the regulation, for example, the at least one heater voltage, does not depart from a corridor around a pilot control value.

(e) Shutting down the regulation, for example, the heating regulation, and switching over to control only, for example, pilot control only, for example, if the at least one checked parameter, for example, the at least one control variable and/or manipulated variable, exceeds or falls below a limiting value. For example, shutting down of the heating regulation and switching over to pilot control only may be provided if the sensor element internal resistance is implausibly high, to prevent the heating regulation from increasing the heater voltage to impermissibly high values.

(f) Shutting down an optional integral component of the regulation, if the at least one parameter reaches, exceeds, or falls below a limiting value. For example, a shutdown of an integral component may be provided if the sensor element internal resistance is implausibly low, for example, to prevent a possibly erroneously taught integral component from resulting in an increase of the heater voltage, although the sensor element already has an excessively high temperature.

Above-mentioned embodiments (a) through (f) may also be combined with one another as desired in pairs or in groups and/or may be combined with other embodiments of the present invention.

The above-described variables used in the proposed method, in particular the controlled variable or its actual value, the at least one parameter, and the at least one control variable, may be detected and/or provided in various ways. In this case, these may be actual, measured variables, which may also be subjected to post-processing, however, for example, signal conditioning in the form of filtering or similar methods. A time curve of these variables may optionally also be recorded and/or used. Alternatively or additionally, the mentioned variables, in particular the actual value and/or the at least one optional control variable, may in turn also be modeled variables, which may be determined, for example, with the aid of one or more simulation methods. In this way, for example, a heater voltage, a heating power, a sensor element internal resistance, temperatures (for example, an exhaust gas temperature and/or a pipe wall temperature and/or other temperatures), an engine operating point (for example, an engine speed, an air quantity, or similar variables which characterize the engine operating point), an exhaust gas mass flow rate and/or exhaust gas volume flow rate, a time curve, or similar variables may be incorporated into the proposed method for setting the temperature. The proposed method and the proposed device may generally be used in particular in temperature-regulated exhaust gas sensors of any type, in particular discrete-level sensors, broadband sensors, or other heatable exhaust gas sensors, in particular sensor elements having the characteristic of a high heating power reserve, which may result in destruction of the sensor element by overheating in the case of heating in the vehicle electrical system voltage range which is permissible in principle. However, the present invention may also be used for maintaining temperature corridors below a damage limit, for example, in $NO_x$ sensors, which have a maximum functional accuracy at low operating temperatures. The present invention is usable in particular, but not exclusively, in the automotive field, no limitation existing with regard to the vehicle segments, the exhaust gas composition, or the target market.

DETAILED DESCRIPTION OF THE INVENTION

Figure 1:
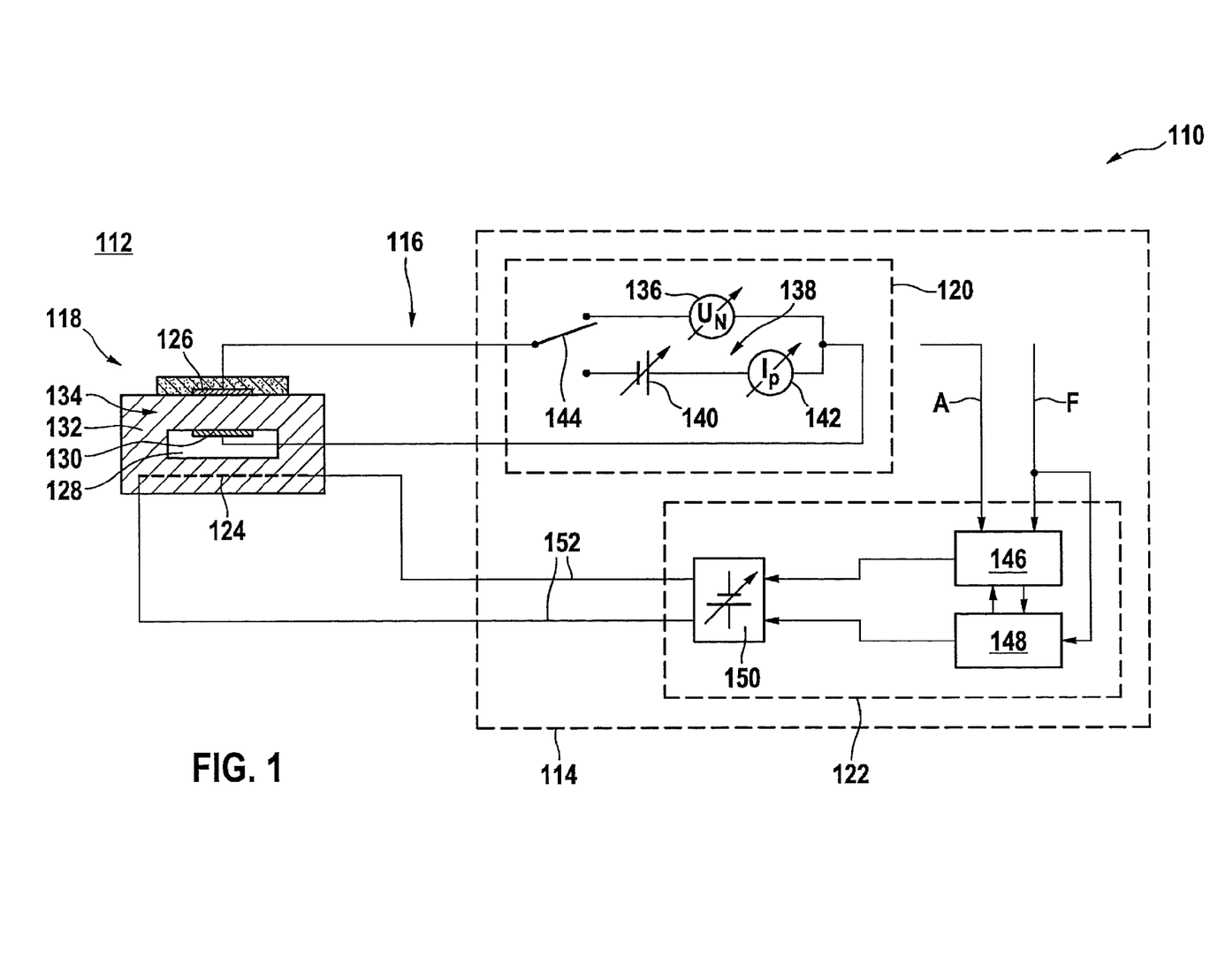
FIG. 1 shows an exemplary embodiment of a sensor device according to the present invention.
Figure 2:
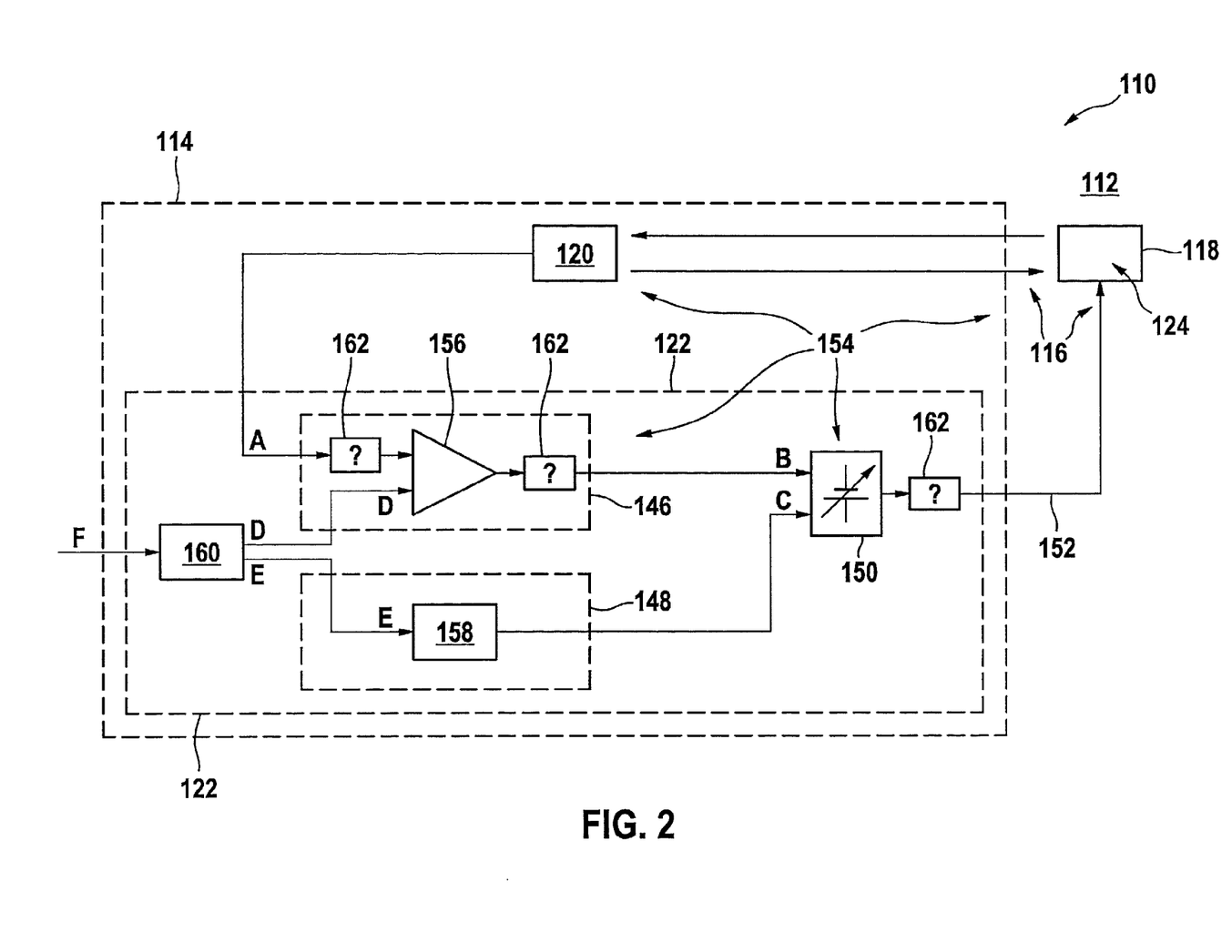
FIG. 2 shows a schematic view of further possible details of a sensor device according to the present invention.

FIG. 1 shows a first exemplary embodiment of a schematic embodiment of a sensor device 110 according to the present invention for detecting at least one characteristic of a gas in a measuring gas chamber 112. FIG. 2 shows another exemplary embodiment. Both exemplary embodiments are essentially described jointly hereafter. Sensor devices 110 each include an activation device 114 and at least one sensor element 118, which is connected to activation device 114 via one or more interfaces 116. Activation device 114 may also be entirely or partially integrated into sensor element 118 itself, however. Activation device 114 is designed as a unit in the illustrations in FIGS. 1 and 2. However, it may also be designed decentrally and may also be implemented entirely or partially in an engine controller, for example. Activation device 114 includes a sensor activation device 120, which is configured for activating sensor element 118 for detecting the at least one characteristic and/or for detecting corresponding signals. Furthermore, activation device 114 includes a heater activation device 122, which is configured for activating at least one heating device 124 of the sensor element, for example, to apply heating energy thereto, for example, in the form of a heater voltage and/or a heater current, which may be designed as continuous or also pulsed. While FIG. 1 shows possible details of the embodiment of sensor activation device 120 and sensor element 118, optional details of heater activation device 122 are shown in FIG. 2. Reference may be made hereafter to both figures, which may also be combined.

Sensor element 118 is designed as an example in the illustrated exemplary embodiment as a simple discrete-level sensor having an outer electrode 126 facing toward measuring gas chamber 112 and a reference electrode 130 situated in reference gas chamber 128, the electrodes being connected to one another via a solid electrolyte 132, for example, yttrium-stabilized zirconium oxide, and form a cell 134. Other structures of sensor element 118 are also possible, however.

In the exemplary embodiment shown in FIG. 1, sensor activation device 120 includes a measuring device 136, to detect a Nernst voltage $U_N$ on cell 134. Furthermore, sensor activation device 120 includes, as an example and optionally, an internal resistance measuring device 138, which may be connected in parallel to measuring device 136 and which may include a pump current source and/or pump voltage source 140 and a pump current measuring device 142, which is connected in series thereto, for example. Furthermore, a switch 144 may be provided, so that a pump voltage pulse and/or pump current pulse may be briefly output to cell 134 with the aid of internal resistance measuring device 138, in order, through a corresponding current measurement of pump current $I_p$, to determine the internal resistance of cell 134, which may in turn be a measure of the temperature of sensor element 118 and may therefore be used directly or indirectly as an actual value (identified in FIG. 1 and in FIG. 2 with "A") of a controlled variable, for example.

Reference is made hereafter to FIG. 2 as an example for possible embodiments of heater activation device 122. It is apparent therefrom that in the illustrated exemplary embodiment, heater activation device 122 may be designed as multipart in particular and may include, for example, at least one regulating device 146 and optionally at least one control device 148. Furthermore, heater activation device 122 may include at least one final control element 150. This final control element 150 may be configured, for example, in accordance with a manipulated variable B provided by regulating device 146 and/or a control manipulated variable C provided by optional control device 148, which may also be referred to as a pilot control variable, to provide electrical power to heating device 124 via one or more heater lines 152. Only one final control element 150 is shown in FIG. 2. However, multiple final control elements may also be provided. Thus, for example, regulating device 146 and control device 148 may have their own, separate final control elements 150, whose output signals may subsequently be combined.

Regulating device 146, final control element 150, sensor element 118, and sensor activation device 120 may jointly form a control loop 154. Regulating device 146 may include a comparison unit 156, in which actual value A of the controlled variable is compared to a setpoint value D of the controlled variable, in order to ascertain manipulated variable B therefrom. It is to be noted that regulating device 146 may additionally include further elements. Control device 148 may include in particular a control final control element 158, with the aid of which control manipulated variable C may also be formed from a reference variable E. Manipulated variable B and control manipulated variable C may be superimposed on one another, which may take place sequentially or also in parallel. This is shown very schematically in FIG. 2. For example, these signals may be added. Alternatively, as described above, different final control elements 150 may also be used for regulating device 146 and control device 148.

To predefine setpoint value D and/or reference variable E, heater activation device 122 may also include a controller 160 indicated in FIG. 2. At least one control variable may be applied thereto, which is identified by F in FIGS. 1 and 2 and which characterizes an influence of surroundings of sensor element 118 on the temperature of sensor element 118. Reference may be made to the above description for possible embodiments of this control variable F. In particular, temperatures of the surroundings of sensor element 118, for example, gas temperatures and/or pipe wall temperatures, and/or a parameter which characterizes a flow of the gas, may be incorporated here. Controller 160, optionally in consideration of this at least one control variable, may predefine reference variable E and therefore influence the pilot control with the aid of control device 148. Alternatively or additionally, actual value E may also be predefined by controller 160. The selection of reference variable E and/or setpoint value D may take place, for example, by using corresponding selection algorithms, for example, by characteristic curve maps, selection functions, or the like. Controller 160 may include, for example, at least one data processing device and/or at least one storage element, with the aid of which the selection algorithms are implementable.

Furthermore, the heater activation device may include one or more monitoring elements 162, which are indicated as examples in FIG. 2. They may be situated at various points and may also be entirely or partially combined with controller 160, however. These monitoring elements 162 are configured to carry out the above-described at least one monitoring step, in which at least one parameter used to set the temperature, in the illustrated exemplary embodiment parameters A, B and optionally the heater power provided by final control element 150 (for example, the heater current, the heater voltage, or similar parameters) may be checked and influenced if necessary. Reference may be made to the above description for further details.

Figure 3:
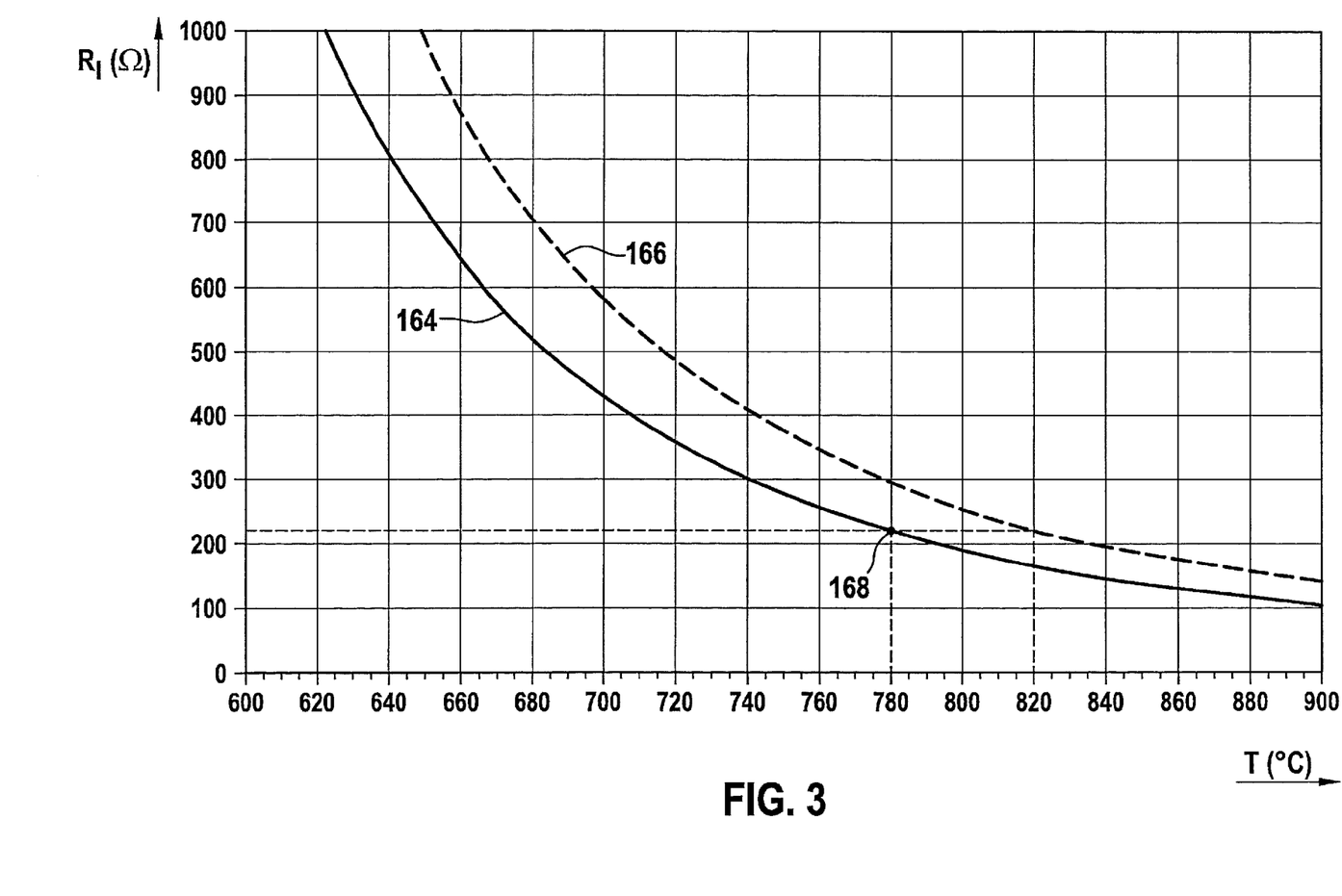
FIG. 3 shows an example of an aging-related internal resistance characteristic curve shift, which may be compensated for with the aid of the proposed method.

With the aid of the above-described method and, for example, with the aid of one or more of sensor devices 110 described in FIGS. 1 and 2, for example, an effect described in FIG. 3 may be counteracted. Thus, in FIG. 3, internal resistances $R_I$ of a Nernst cell, for example, cell 134 of sensor element 118 according to FIG. 1, for typical sensor elements 118 are plotted as a function of temperature T of a ceramic solid electrolyte 132. Curve 164 shows a new sensor element, while in contrast curve 166 shows the behavior of an aged sensor element. A desirable operating point of a new sensor element is identified by 168 in FIG. 2. Thus, the temperature of the sensor element is ideally to be set to 780° C., for example, which corresponds in a new sensor element to an internal resistance of 220Ω. If this internal resistance $R_I$ is used as the controlled variable, curve 166 of the aged sensor element, in contrast, shows that in the aged sensor element this internal resistance of 220Ω corresponds to a temperature of 820° C., i.e., a deviation of 40° C. This deviation is sensitively noticeable in the sensor accuracy. In order to reach this temperature of 820° C., however, a significantly higher heating power is necessary. The regulation described in FIG. 2, for example, would therefore provide higher values, for example, at the output of comparison unit 156 and/or at the output of final control element 150, than in comparison to the new sensor element. Such a deviation may be detected by one or more monitoring elements 162, and if necessary appropriate countermeasures may be taken by correction in the monitoring step and by appropriate influence of the manipulated variable.

Figure 4:
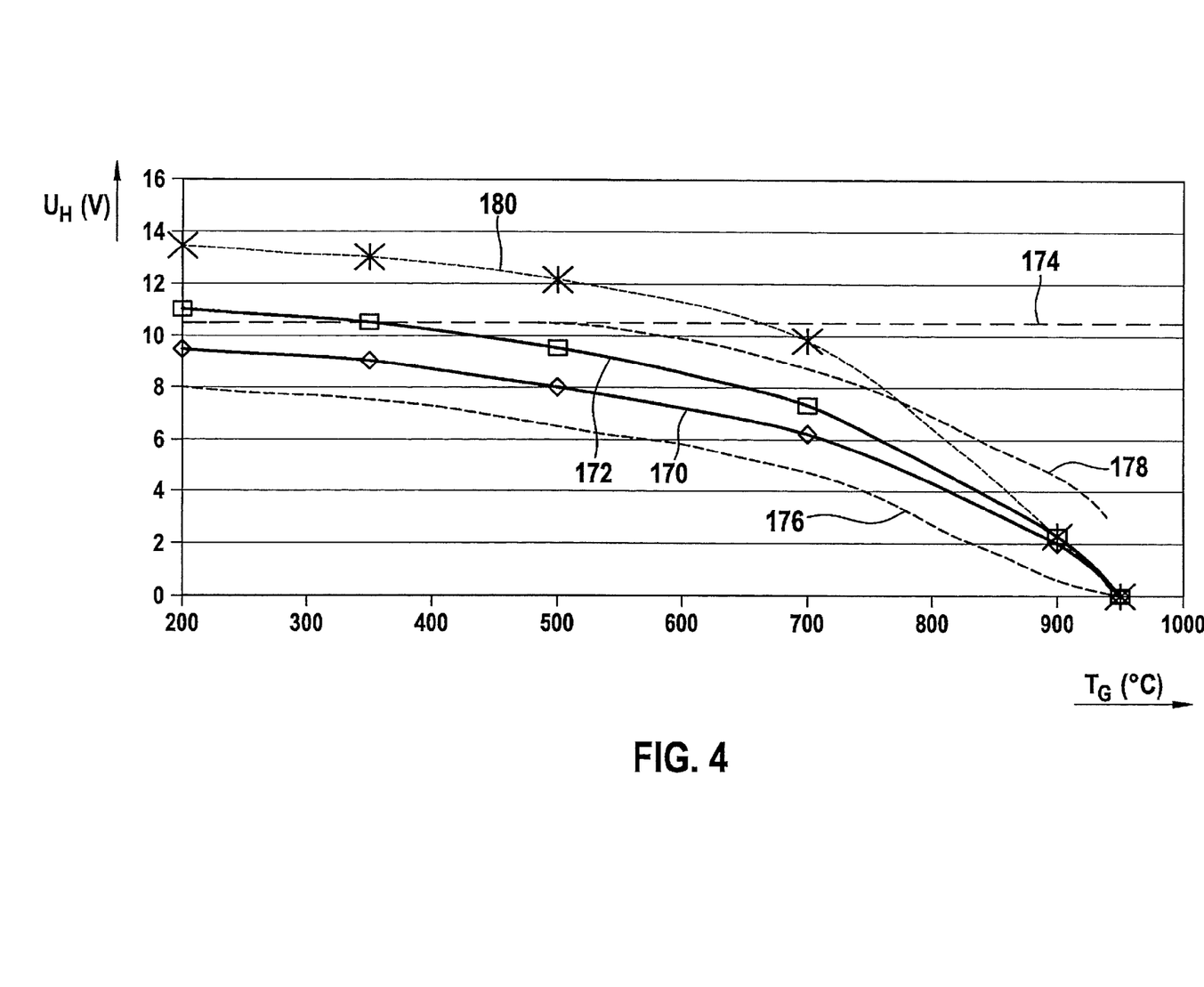
FIG. 4 shows an exemplary embodiment of possible limitations of a heater voltage with the aid of the proposed method.

In FIG. 4, various possible examples are described of a superposition of a control and a regulation, with simultaneous implementation of the above-described method and in consideration of an exhaust gas temperature $T_G$ as a control variable. In this case, a variable which characterizes the heating power of heating device 124, and which is identified here by $U_H$, is plotted on the vertical axis. This may be the heater voltage in this case, for example, other variables which characterize the heating power also being able to be plotted, however. A pilot control takes place initially, for example, with the aid of control device 148. The characteristic curves plotted in FIG. 4 show which heating power $U_H$ must be provided by activation device 114 at which temperature of the gas in measuring gas chamber 112 to keep the sensor element at a constant temperature, for example, 780° C. according to FIG. 3. At lower exhaust gas temperatures, a higher heating power is accordingly required than at high exhaust gas temperatures. Curve 170 in turn shows a characteristic curve of a new sensor element, while in contrast curve 172 shows a characteristic curve of an aged sensor element. Such characteristic curves 170, 172 may be stored in controller 160, for example, so that, for example, values D and E in FIG. 2 may be selected accordingly.

The influence of the at least one manipulated variable in the at least one monitoring step, for example, with the aid of monitoring elements 162 in FIG. 2, may take place in various ways shown in FIG. 4. For example, an absolute cap 174 may be placed on a fixedly predefined limiting value of the heating power. Alternatively or additionally, for example, however, dynamic limiting values may also be predefined, for example, in the form of a lower limiting value 176 and/or an upper limiting value 178, which may be situated around characteristic curves 170, 172, for example. For example, upon reaching these limiting values 174, 176, 178, default values may be assumed and/or the heating power may be turned off and/or one or more others of the above-described influencing measures may be taken. Finally, curve 180 shows an error case, in which the heating power would greatly exceed absolute cap 174 in the range of exhaust gas temperatures less than approximately 670° C.

What is claimed is:

1. A method for setting a temperature of a sensor element which is heatable with the aid of a heating device, wherein the sensor element is configured for detecting a fraction of at least one gas component in a gas mixture in a measuring gas chamber, the method comprising:
   performing a regulation of the heating device, wherein the regulation includes:
   a) detecting at least one actual value of at least one controlled variable of the sensor element;
   b) ascertaining a setpoint value of the at least one controlled variable;
   c) generating at least one manipulated variable of the heating device with the aid of a comparison of the setpoint value and the actual value of the at least one controlled variable; and
   d) performing at least one monitoring step in which at least one parameter used for setting the temperature of the sensor is checked, wherein the at least one manipulated variable is influenced as a function of the check.

2. The method as recited in claim 1, wherein the manipulated variable is generated by comparing the setpoint value to the actual value.

3. The method as recited in claim 1, wherein the manipulated variable is processed by an at least on final control element before application to the heating device.

4. The method as recited in claim 3, wherein the at least one final control element is one of a heating voltage generator and an amplifier.

5. The method as recited in claim 1, further comprising:
detecting at least one control variable characterizing an influence of surroundings of the sensor element on the temperature of the sensor element, wherein the at least one control variable includes one of: an ambient temperature of the sensor element; an operating parameter of an internal combustion engine which uses the gas; a parameter which characterizes a gas flow arising in the surroundings of the sensor element; a parameter which characterizes a temperature arising in the surroundings of the sensor element; an engine speed; or an engine load state.

6. The method as recited in claim 5, wherein the at least one controlled variable includes one of: at least one internal resistance of the sensor element; a temperature of the sensor element; a voltage between at least two electrodes of a Nernst cell of the sensor element; a current between at least two electrodes of a pump cell of the sensor element; or an electrical resistance of a conductive structure of the sensor element.

7. The method as recited in claim 5, wherein the manipulated variable includes one of: a heating voltage applied to the heating device; a heating power applied to the heating device;
a heating current applied to the heating device; or a parameter of a pulse width modulation of a heating power applied to the heating device.

8. The method as recited in claim 5, wherein the parameter checked in the monitoring step includes one of a: the actual value of the controlled variable; the setpoint value of the controlled variable; the manipulated variable; or the control variable characterizing an influence of the surroundings of the sensor element on the temperature of the sensor element.

9. The method as recited in claim 5, wherein the check of the parameter in the monitoring step includes at least one of:
a comparison of the parameter with one of a fixedly or dynamically predefined threshold value;
a comparison of a time variation of the parameter over a measuring period of time with a predefined maximum variation; and
a comparison of a time curve of the parameter to at least one setpoint curve.

10. The method as recited in claim 5, wherein the influence of the manipulated variable in the monitoring step includes at least one of:

rejecting at least one measured value of the parameter for influencing the manipulated variable;
filtering of the actual value and influencing of the manipulated variable;
averaging of the actual value and influencing the manipulated variable;
limiting of the manipulated variable by one of a predefined minimum value or maximum value;
setting the manipulated variable to a default value;
decreasing the manipulated variable by one of a predefined absolute value or a correction factor;
converting the manipulated variable into a changed manipulated variable with the aid of at least one correction function;
changing at least one control loop for setting the temperature; and
ending down the regulation.

11. The method as recited in claim 5, further comprising:
performing a control of the heating device, wherein the regulation of the heating device is at least temporarily superimposed on the control.

12. The method as recited in claim 11, wherein the control of the heating device takes place in consideration of the control variable.

13. The method as recited in claim 11, wherein the ascertainment of the setpoint value and the control of the heating device take place in consideration of the control variable.

14. A sensor device detecting a fraction of at least one gas component in a gas mixture in a measuring gas chamber, comprising:
at least one sensor element for detecting the fraction of at least one gas component in the gas mixture;
at least one heating device for heating at least a part of the sensor element; and
at least one activation device configured to perform a regulation of the heating device, wherein the regulation includes:
a) detecting at least one actual value of at least one controlled variable of the sensor element;
b) ascertaining a setpoint value of the at least one controlled variable;
c) generating at least one manipulated variable of the heating device with the aid of a comparison of the setpoint value and the actual value of the at least one controlled variable; and
d) performing at least one monitoring step in which at least one parameter used for setting the temperature of the sensor is checked, wherein the at least one manipulated variable is influenced as a function of the check.

* * * * *